US011377679B2

(12) United States Patent
Kwon et al.

(10) Patent No.: US 11,377,679 B2
(45) Date of Patent: Jul. 5, 2022

(54) MULTI-WELL-BASED CELL CULTURE TEST DEVICE FOR RAPID ANTIBIOTIC SUSCEPTIBILITY TESTING

(71) Applicant: QuantaMatrix Inc., Seoul (KR)

(72) Inventors: Sung Hoon Kwon, Seoul (KR); Hyun Yong Jeong, Seoul (KR); Tae Geun Lim, Seoul (KR); Jung Il Choi, Seoul (KR); Eun Guen Kim, Gunpo-si (KR)

(73) Assignee: QUANTAMATRIX INC., Seoul (KR)

( * ) Notice: Subject to any disclaimer, the term of this patent is extended or adjusted under 35 U.S.C. 154(b) by 158 days.

(21) Appl. No.: 16/087,608

(22) PCT Filed: Apr. 17, 2017

(86) PCT No.: PCT/KR2017/004116
§ 371 (c)(1),
(2) Date: Sep. 21, 2018

(87) PCT Pub. No.: WO2017/183875
PCT Pub. Date: Oct. 26, 2017

(65) Prior Publication Data
US 2019/0100786 A1 Apr. 4, 2019

(30) Foreign Application Priority Data

Apr. 21, 2016 (KR) .................. 10-2016-0048829

(51) Int. Cl.
*C12M 3/00* (2006.01)
*B01L 3/00* (2006.01)
(Continued)

(52) U.S. Cl.
CPC ............. *C12Q 1/025* (2013.01); *B01L 3/00* (2013.01); *B01L 3/50255* (2013.01);
(Continued)

(58) Field of Classification Search
CPC ...................... C12M 23/12; B01L 3/50255
See application file for complete search history.

(56) References Cited

U.S. PATENT DOCUMENTS

| 4,247,634 A | 1/1981 | Abdou |
| 5,272,084 A * | 12/1993 | O'Connell ............ C12M 23/08 |
| | | 215/DIG. 3 |

(Continued)

FOREIGN PATENT DOCUMENTS

| EP | 2987851 A1 | 2/2016 |
| JP | 2015029431 A | 2/2015 |

(Continued)

OTHER PUBLICATIONS

Phillip H.Gallo et al, Demonstration of Bacillus Cereus in Orthopedic-Implant-Relate Infection with Use of a Multi-Primer Polymerase Chain Reaction-Mass Spectrometric Assay, The Journal of Bone and Joint Surgery, Aug. 3, 2011, p. e85(1-6), vol. 93-A, The Journal of Bone and Joint Surgery Incorporation; Needham, USA.

(Continued)

*Primary Examiner* — Nathan A Bowers
(74) *Attorney, Agent, or Firm* — STIP Law Group, LLC

(57) ABSTRACT

Provided is a multi-well-based cell culture test device having an array structure of a plurality of aligned well units. Each of the well units includes a first sub-well adapted to accommodate a first fluid, a second sub-well adapted to accommodate a second fluid, and a barrier located between the first sub-well and the second sub-well to partition the first sub-well and the second sub-well. The first sub-well has a recess in the depth direction with respect to its bottom to accommodate a solid thin film formed by solidifying the first fluid. The barrier has such a height that the first fluid does not overflow into the second sub-well when the first fluid is loaded into the first sub-well to fill the recess.

14 Claims, 9 Drawing Sheets

(51) Int. Cl.
*C12Q 1/02* (2006.01)
*C12Q 1/04* (2006.01)
*C12M 1/32* (2006.01)
*C12N 5/00* (2006.01)
*G01N 33/50* (2006.01)
*C12M 1/12* (2006.01)
*C12M 1/00* (2006.01)

(52) U.S. Cl.
CPC ....... *B01L 3/502715* (2013.01); *C12M 23/12* (2013.01); *C12M 23/34* (2013.01); *C12M 25/14* (2013.01); *C12N 5/0068* (2013.01); *C12Q 1/04* (2013.01); *G01N 33/50* (2013.01)

(56) References Cited

U.S. PATENT DOCUMENTS

| | | | | |
|---|---|---|---|---|
| 5,512,476 | A * | 4/1996 | Gordon | B01L 3/502 600/33 |
| 6,039,804 | A * | 3/2000 | Kim | C30B 7/00 117/206 |
| 6,475,760 | B1 * | 11/2002 | Baumann | C12M 35/02 435/173.4 |
| 6,542,293 | B2 * | 4/2003 | Yahiro | B01L 3/5085 250/201.3 |
| 9,260,684 | B1 * | 2/2016 | Egeler | B01L 3/5085 |
| 2008/0207465 | A1 * | 8/2008 | Ravkin | B01L 3/5085 506/9 |
| 2008/0247915 | A1 * | 10/2008 | Cecchi | A01N 1/02 422/400 |
| 2010/0221768 | A1 | 9/2010 | Akai et al. | |
| 2010/0297600 | A1 | 11/2010 | Cecchi | |
| 2011/0104798 | A1 | 5/2011 | Tschumperlin et al. | |
| 2013/0059322 | A1 | 3/2013 | Hung et al. | |
| 2016/0002583 | A1 * | 1/2016 | Hlinka | C12M 23/34 435/305.2 |
| 2017/0226458 | A1 * | 8/2017 | Li | C12M 29/04 |

FOREIGN PATENT DOCUMENTS

| | | |
|---|---|---|
| KR | 200325376 Y1 | 9/2003 |
| KR | 1020130089619 A | 8/2013 |
| KR | 1020140014494 A | 2/2014 |
| KR | 101446526 B1 | 10/2014 |
| KR | 1020150101178 A | 9/2015 |
| KR | 101711105 B1 | 3/2017 |
| WO | WO8902927 A1 | 4/1989 |
| WO | WO9100903 A1 | 1/1991 |
| WO | WO03078565 A1 | 9/2003 |
| WO | WO2011161480 A | 12/2011 |
| WO | WO2010047132 A1 | 3/2012 |

OTHER PUBLICATIONS

Gregory Anderston et al, Intraceullar Bacterial Biofilm-Like Pods in Urinary Tract Infections, Science, Jul. 4, 2003, pp. 105-108, vol. 301, American Association for the Advancement of Science, Washington DC, USA.
International Search Report of PCT/KR2017/004116, dated Aug. 31, 2017, English translation.
The extended European search report of 17786143.2, dated Oct. 2, 2019.

* cited by examiner

[Fig. 1]
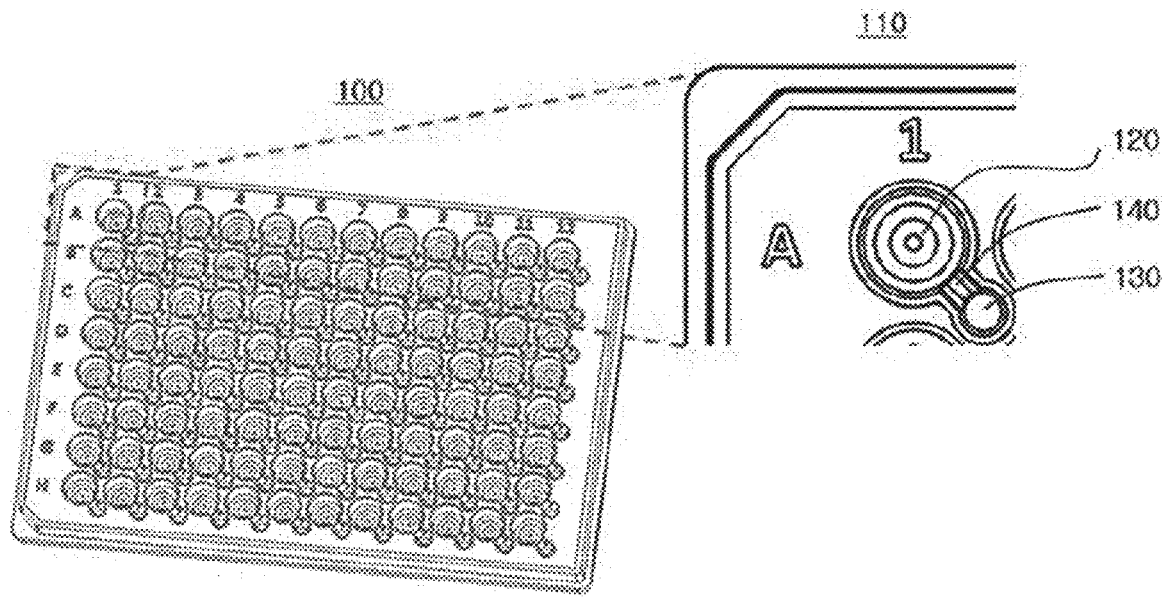
[Fig. 2]
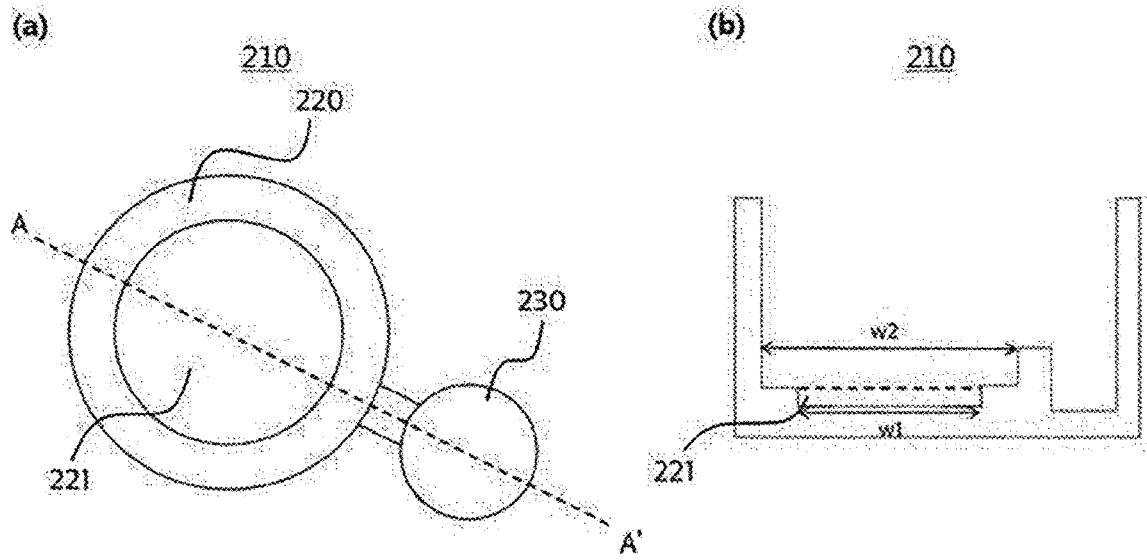

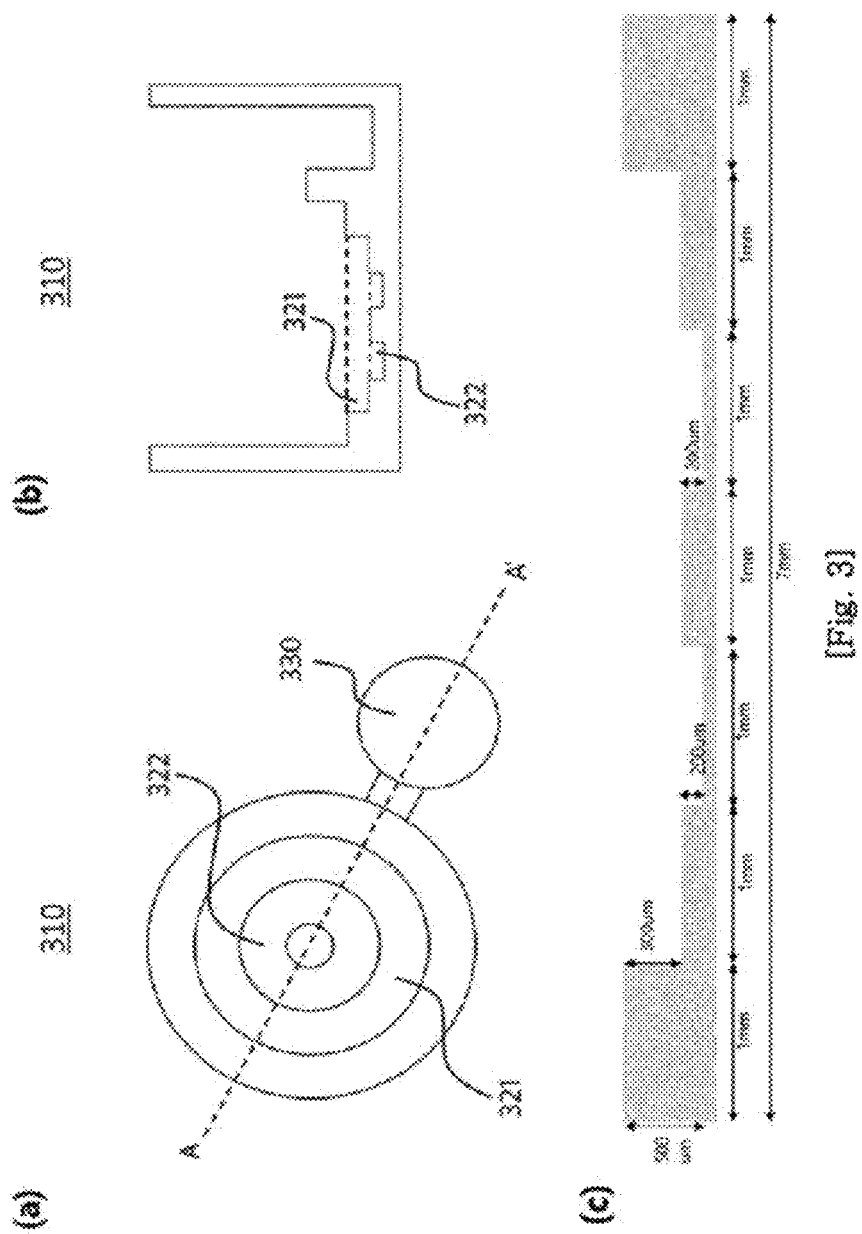

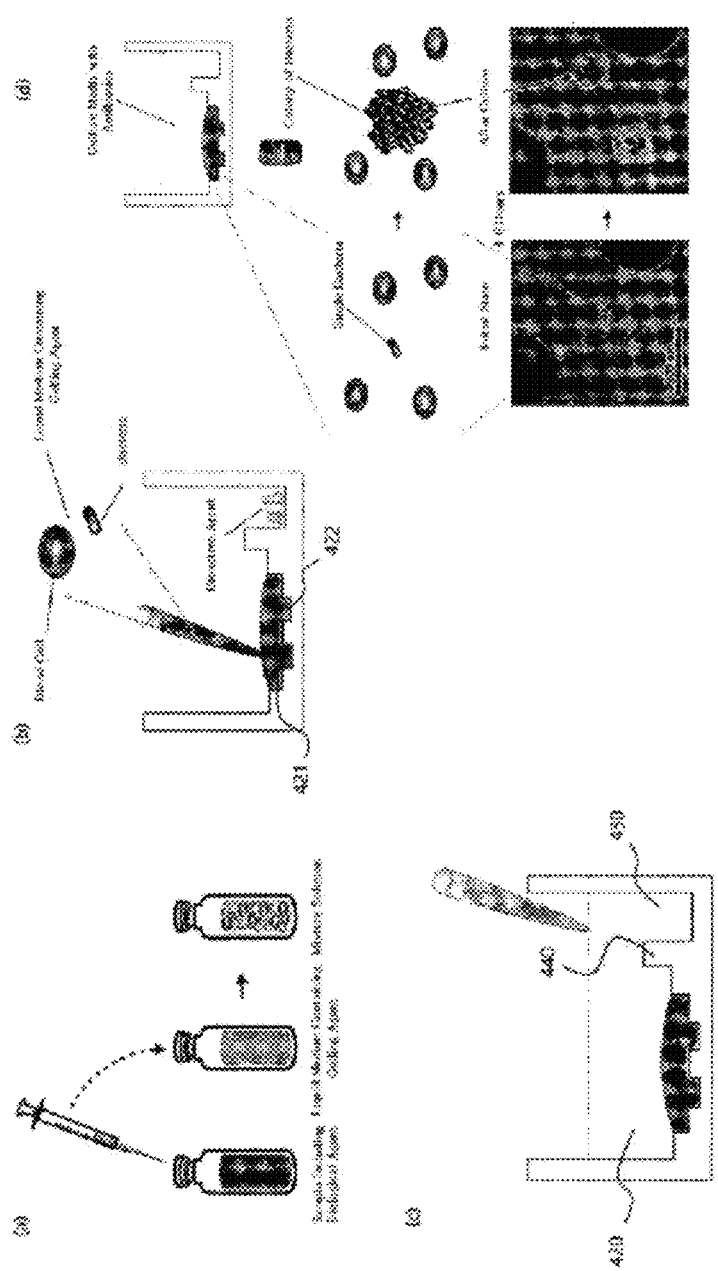
[Fig. 4]

[Fig. 5]
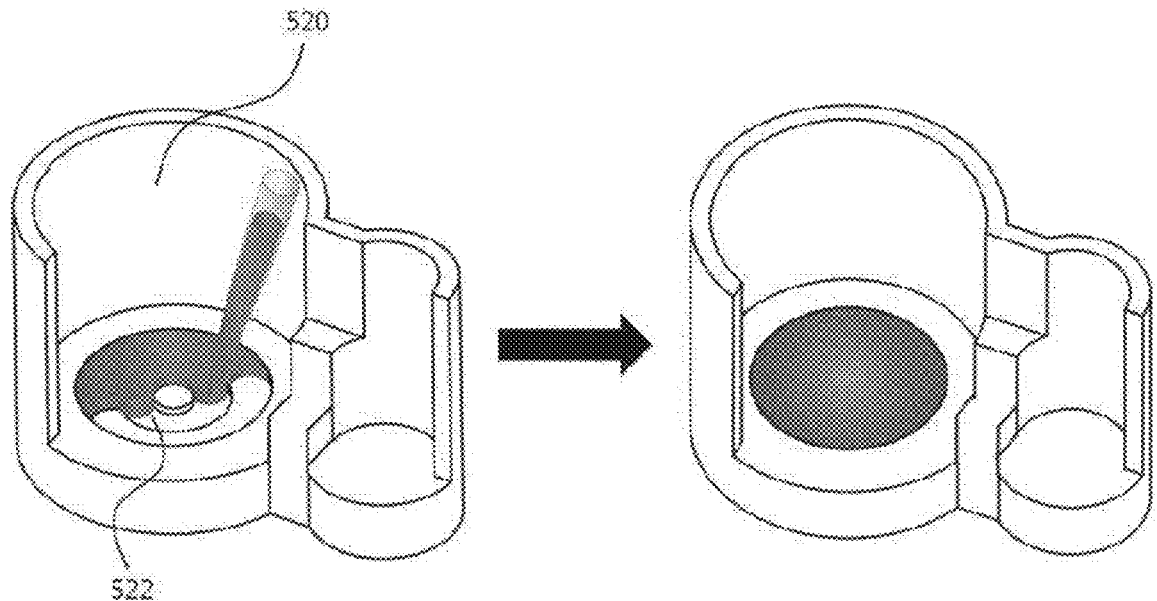
[Fig. 6]
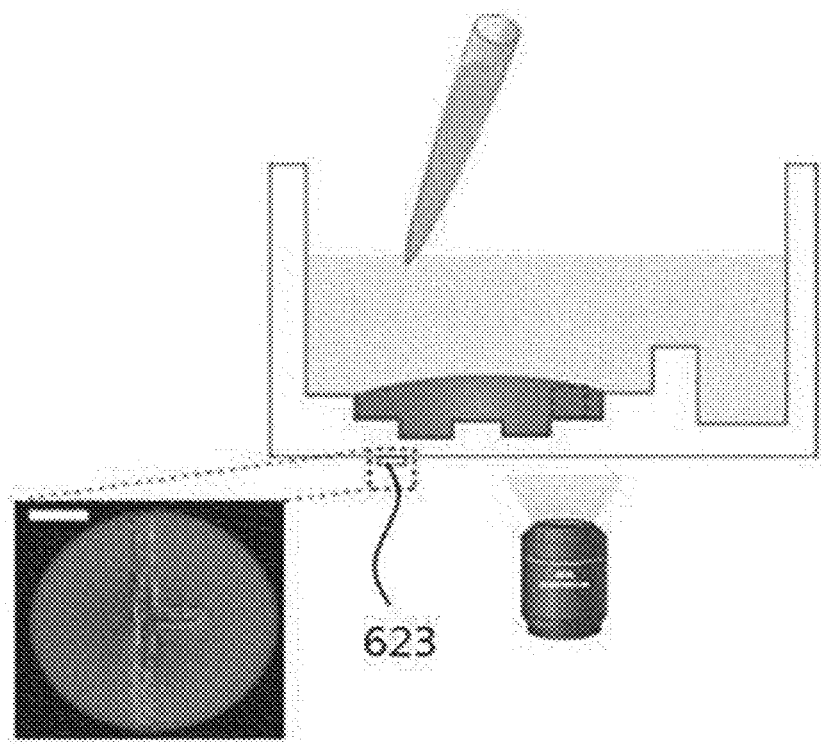

[Fig. 7]
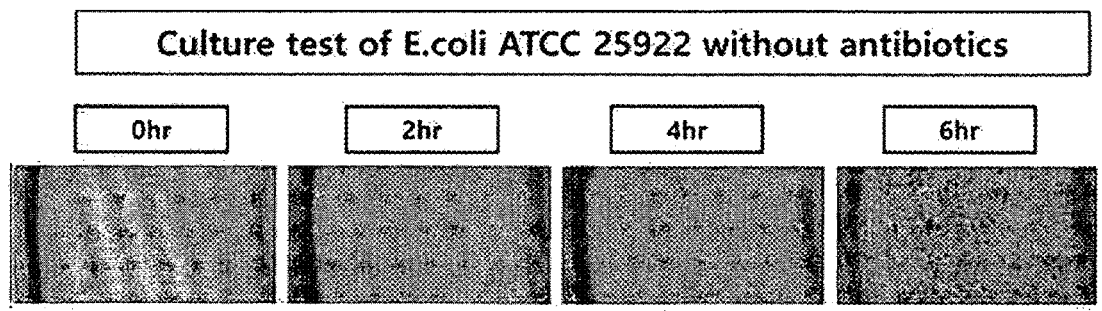
[Fig. 8]
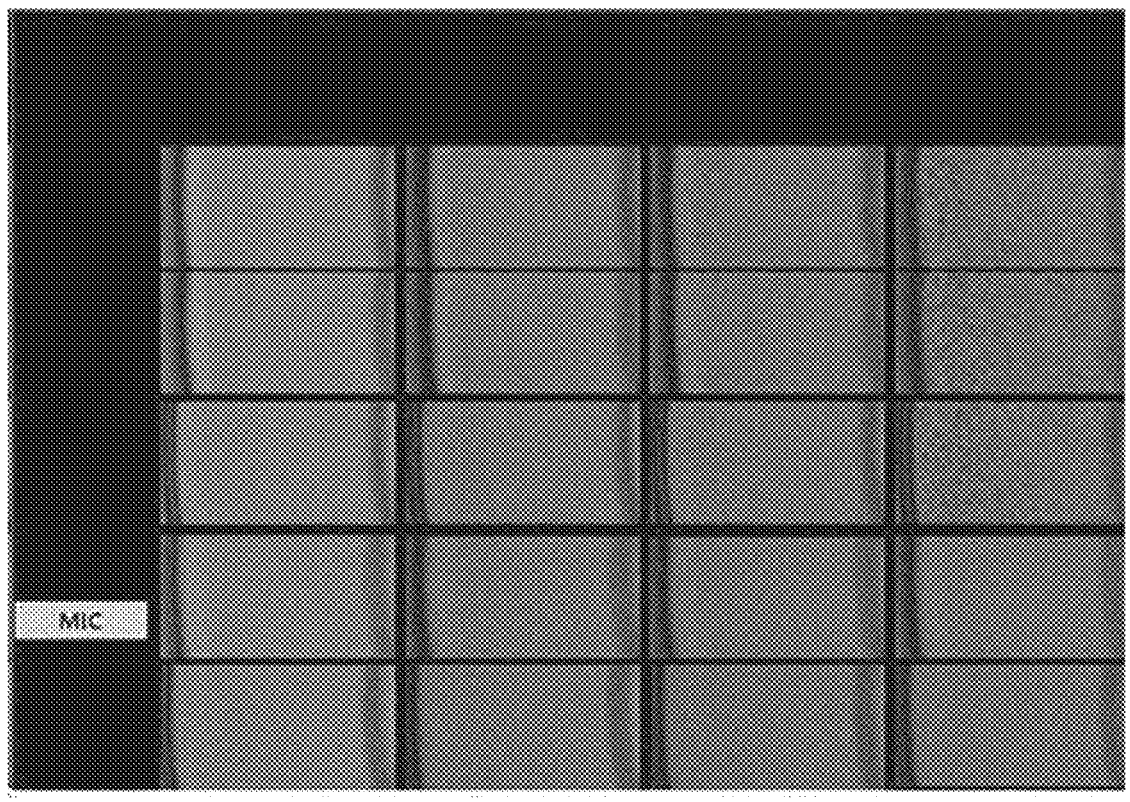

[Fig. 9]
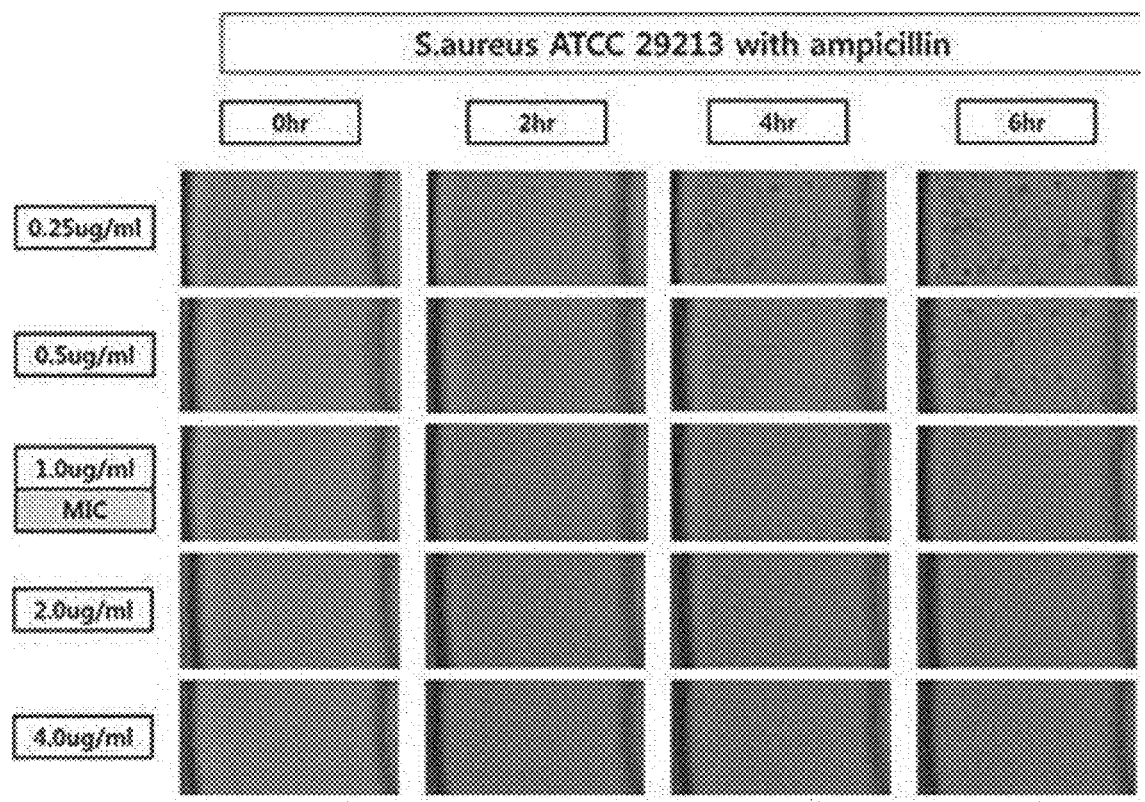

[Fig. 10]
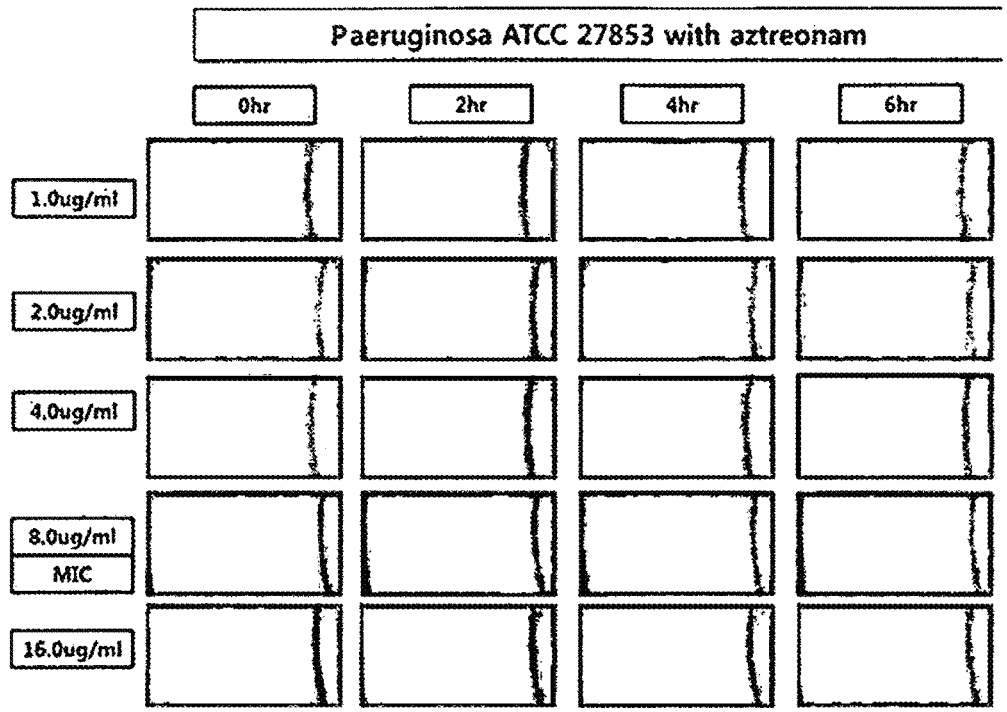
[Fig. 11]
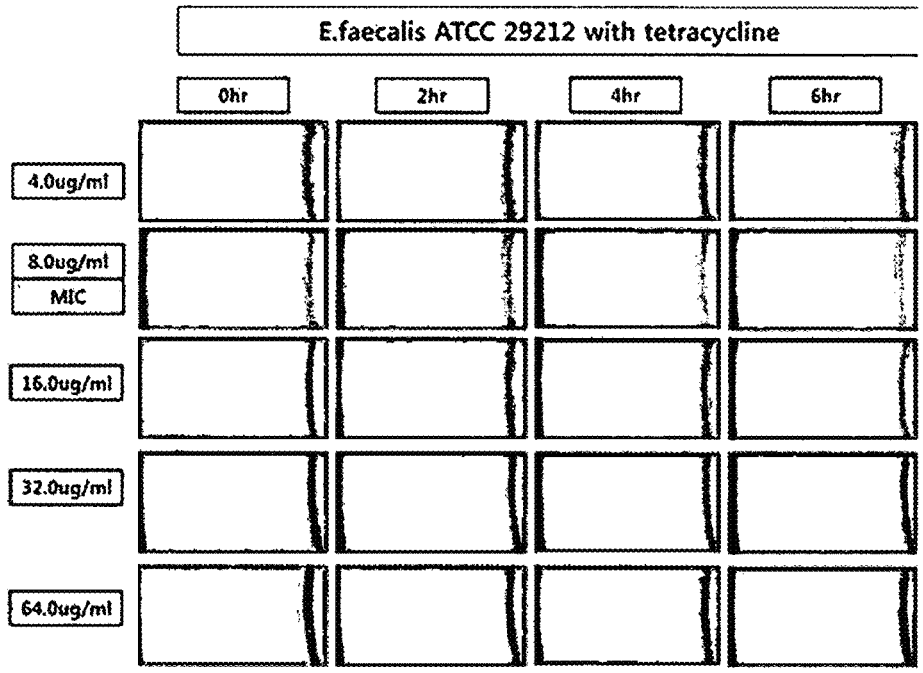

| Antibiotic | Gram negative | | | Total Test Range | K.pneumoniae BMD | K.pneumoniae DRAST | K.pneumoniae BMD | K.pneumoniae DRAST | E.aerogenes BMD | E.aerogenes DRAST | P.aeruginosa BMD | P.aeruginosa DRAST |
|---|---|---|---|---|---|---|---|---|---|---|---|---|
| | Enterobac. cloacae | Pseudomonas aeruginosa | Acinetobacter | | | | | | | | | |
| Piperacillin | 16,128 | 16,128 | 16,128 | 16,128 | <16 | <16 | <16 | <16 | <16 | <16 | <16 | <16 |
| Amoxicillin Clavulanic acid | 8/4, 32/16 | - | - | 8/4, 32/16 | 8/4 | <8/4 | <8/4 | <8/4 | >32/16 | >32/16 | >32/16 | >32/16 |
| Meropenem | 1,4 | 2,8 | 2,8 | 1,8 | <1 | <1 | <1 | <1 | <1 | <1 | <1 | <1 |
| Amikacin | 16,64 | 16,64 | 16,64 | 16,64 | <16 | <16 | <16 | <16 | <16 | <16 | <16 | <16 |
| Piperacillin Tazobactam | 16/4,128/4 | 16/4,128/4 | 16/4,128/4 | 16/4,128/4 | <16/4 | <16/4 | <16/4 | <16/4 | <16/4 | <16/4 | <16/4 | <16/4 |
| Fosfomycin | 64, 256 | - | - | 64, 256 | - | - | - | - | - | - | - | - |
| Ticarcillin | 16, 128 | 16,128 | 16, 128 | 16,128 | <16 | <16 | <16 | <16 | <16 | <16 | 32 | <16 |
| Ticarcillin Clavulanic acid | 16/2,128/2 | 16/2,128/2 | 16/2,128/2 | 16/2,128/2 | <16/2 | <16/2 | <16/2 | <16/2 | <16/2 | <16/2 | 32/2 | <16/2 |
| Cefotaxime | 1,4 | - | 8,64 | 1,64 | <1 | <1 | <1 | <1 | <1 | <1 | 16 | <1 |
| Ceftazidime | 4,16 | 8,32 | 8,32 | 4,32 | <4 | <4 | <4 | <4 | <4 | <4 | <4 | <4 |
| Cefepime | 2,16 | 8,32 | 8,32 | 2,32 | <2 | <2 | <2 | <2 | <2 | <2 | <2 | <2 |
| Aztreonam | 4,16 | 8,32 | - | 4,32 | <8 | <8 | <8 | <8 | <8 | <8 | 32 | <8 |
| Gentamicin | 4,16 | 4,16 | 4,16 | 4,16 | - | - | - | - | <2 | <2 | <2 | - |
| Colistin | - | 2,8 | 2,4 | 2,8 | <2 | 4 | <2 | 4 | <2 | 8 | <2 | 8 |
| Tobramycin | 4,16 | 4,16 | 4,16 | 4,16 | 16 | 16 | <4 | <4 | <4 | <4 | <4 | <4 |
| Trimethoprim Sulfamethoxazole | 2/38, 4/76 | - | 2/38, 4/76 | 2/38, 4/76 | <2/38 | <2/38 | <2/38 | <2/38 | <2/38 | <2/38 | 4/76 | <2/38 |
| Imipenem | 1,4 | 2,8 | 2,8 | 1,8 | <1 | <1 | <1 | <1 | 2 | 4 | 2 | 2 |
| Ciprofloxacin | 1,4 | 1,4 | 1,4 | 1,4 | <1 | <1 | <1 | <1 | <1 | <1 | <1 | <1 |

[Fig. 12]

| Antibiotic | Gram positive | | | | | | | | |
|---|---|---|---|---|---|---|---|---|---|
| | Staphylococcus | Enterococcus | S. epidermis | | E. faecium | | E. faecium | | S. haemolyticus | |
| | | | BMD | DRAST | BMD | DRAST | BMD | DRAST | BMD | DRAST |
| Rifampin | 1,4 | 1,4 | <1 | <1 | 4 | 4 | 4 | >4 | <1 | <1 |
| Oxacillin | 2,4 | | 4 | <2 | >4 | >4 | >4 | >4 | <2 | <2 |
| Erythromycin | 0.5,8 | 0.5,8 | >8 | >8 | >8 | >8 | >8 | >8 | <0.5 | <0.5 |
| Ampicillin | 0.12,0.25 | 8,16 | 16 | 8 | >16 | >16 | >16 | >16 | <0.12 | 8 |
| Ciprofloxacin | 1,4 | 1,4 | 4 | >4 | >4 | >4 | >4 | >4 | 2 | 4 |
| Penicillin | 0.12,0.25 | 8,16 | 16 | 8 | >16 | >16 | >16 | >16 | 8 | 8 |
| Tetracycline | 4,16 | 4,16 | <4 | <4 | <4 | <4 | <4 | <4 | 16 | >16 |
| Clindamycin | 0.5,4 | | <0.5 | <0.5 | >4 | >4 | >4 | >4 | 2 | <0.5 |
| Linezolid | 4,8 | 2,8 | 4 | <2 | <2 | <2 | 4 | <2 | <2 | <2 |
| Levofloxacin | 1,4 | 2,8 | 4 | >8 | >8 | >8 | >8 | >8 | <1 | 2 |
| Trimethoprim sulfamethoxazole | 2/38, 4/76 | | <2/76 | >4/76 | <2/76 | >4/76 | <2/76 | >4/76 | <2/76 | <2/76 |
| Vancomycin | 2,16 | 4,32 | — | <2 | >32 | >32 | 32 | <2 | <2 | <2 |
| Imipenem | 2,4 | | <2 | <2 | >4 | >4 | >4 | >4 | 4 | <2 |

[Fig. 13]

MULTI-WELL-BASED CELL CULTURE TEST DEVICE FOR RAPID ANTIBIOTIC SUSCEPTIBILITY TESTING

CROSS-REFERENCE TO RELATED APPLICATIONS

This application is the U.S. National Phase under 35 U.S.C. § 371 of International Application No. PCT/KR2017/004116 filed on Apr. 17, 2017, which in turn claims the benefit of Korean Application No. 10-2016-0048829, filed on Apr. 21, 2016, the disclosures of which are incorporated by reference into the present application.

TECHNICAL FIELD

The present disclosure relates generally to a multi-well-based cell culture test device.

BACKGROUND ART

In general, the responses of cells to a drug are observed by placing the cells in a multi-well plate, injecting the drug in a liquid form, and monitoring time-dependent changes of the cells using an optical measurement system to obtain statistic results. As an antibiotic susceptibility testing method in a solid medium, the Kirby-Bauer (KB)-testing method, in which bacteria are scattered over an agar medium, antibiotic-absorbed papers are placed thereon, and bacterial growth is observed, is known. In the case of microdilution testing in liquid media, a number of automated systems, such as VITEK2, Microscan and Phoenix, have been developed for antibiotic susceptibility testing. Such a system can be used for antibiotic susceptibility testing by placing an antibiotic in millimeter-sized wells, injecting bacteria, together with a liquid medium, into the wells, and statistically monitoring and determining the bacterial growth through turbidity.

When the responses of cells to different drugs are tested using the conventional systems, the cells are placed in a liquid or solid medium, the drugs are mixed with the liquid medium or drug-absorbed paper disks are placed on the solid medium to allow the cells to respond to the drugs, and the cell growth responses to the drugs are determined by turbidity (absorbance) measurement. However, such an approach is dependent on the collection of statistically valid data rather than on changes of single cells, and requires a long incubation time (usually 16-24 hours) because a predetermined number of cells should grow (usually one million cells per ml) in order to obtain statistic results. In this case, it is impossible to monitor changes occurring in single cells against drugs and monitor motile single cells in real time. Further, a great deal of time and labor is required to test the large number of drugs because the individual drugs are injected separately. The KB-test for antibiotic susceptibility testing in solid media basically requires a large number of agar medium plates to test the susceptibility of tens of antibiotics due to the limited number of the drugs that can be placed on the solid media. VITEK, an automated system developed to minimize testing time, also requires a relatively long time of about 12 hours because the turbidity of bacteria should increase above a predetermined level. Further, since environments for the conventional testing methods are different from in vivo environments, there may be many substantial differences between the test results and phenomena occurring in vivo (Gregory G. Anderson, et al. (2003), "Intracellular Bacterial Biofilm-Like Pods in Urinary Tract Infections", *Science* 301, 105; Gallo et al. (2011), "Demonstration of *Bacillus cereus* in Orthopaedic-Implant-Related Infection with Use of a Multi-Primer Polymerase Chain Reaction-Mass Spectrometric Assay.", J Bone Joint Surg Am, 93).

Therefore, there is a need to develop more accurate and rapid technologies for antibiotic susceptibility testing than the prior art.

DETAILED DESCRIPTION OF THE INVENTION

Means for Solving the Problems

According to one aspect of the present invention, there is provided a multi-well-based cell culture test device having an array structure of a plurality of aligned well units, each of which includes a first sub-well adapted to accommodate a first fluid, a second sub-well adapted to accommodate a second fluid, and a barrier located between the first sub-well and the second sub-well to partition the first sub-well and the second sub-well, wherein the first sub-well has a recess in the depth direction with respect to its bottom to accommodate a solid thin film formed by solidifying the first fluid and the barrier has such a height that the first fluid does not overflow into the second sub-well when the first fluid is loaded into the first sub-well to fill the recess.

According to one embodiment, at least one micropatterned groove may be formed at the bottom of the recess.

According to one embodiment, the micropatterned groove may be provided in plurality and the micropatterned grooves may be channels arranged concentrically around the center of the recess.

According to one embodiment, at least a portion of the bottom of the recess may be made of an optically transparent material such that analytes present in the first fluid are observable through the bottom of the recess.

According to one embodiment, a focus mark may be provided on the underside of the first sub-well to provide information on the position of analytes.

According to one embodiment, the ratio of the width of the recess to the width of the first sub-well may be from 0.2:1 to 0.99:1.

According to one embodiment, the dimensions of each of the well units may correspond to those of each well of a commercial multi-well plate.

According to one embodiment, the well units may be arranged in a 1×1, 1×2, 1×4, 2×4, 4×6, 12×8, 24×16 or 48×32 matrix.

According to one embodiment, the first fluid may be a mixture solution of a gelling agent-containing liquid medium and a biological agent.

According to one embodiment, the second fluid may be a solution containing a bioactive agent.

According to one embodiment, the second sub-well may include a bioactive agent in a solid form.

According to one embodiment, the second fluid may be a solvent capable of dissolving the bioactive agent.

According to a further aspect of the present invention, there is provided a cell analysis method using the cell culture test device, the method including (a) providing a mixture solution of a gelling agent-containing liquid medium and a biological agent to a recess formed at the bottom of the first sub-well, (b) solidifying the mixture solution to form a solid thin film immobilized with the biological agent, (c) providing a solution containing a bioactive agent to the second sub-well or providing the second sub-well including a bioactive agent in a solid form with a solvent capable of dissolving the bioactive agent, (d) loading the bioactive agent-containing solution or the solvent capable of dissolving the bioactive agent in such an amount that the solution or the solvent crosses over the barrier, to allow the bioactive agent to diffuse into the solid thin film in the first sub-well, and (e) observing responses of the biological agent to the bioactive agent.

According to one embodiment, time-dependent changes of the biological agent may be measured using an imaging system.

According to one embodiment, the responses of the biological agent may be observed on a single cell colony basis.

According to one embodiment, the mixture solution may be prepared by collecting the biological agent positive for bacterial infection and diluting the biological agent with the gelling agent-containing liquid medium.

According to one embodiment, the liquid medium may include a medium stimulating the division of particular cells.

According to one embodiment, the method may further include (f) observing changes of the biological agent responding to the bioactive agent on a single cell colony basis to determine the minimum inhibitory concentration (MIC) or minimum biofilm eradication concentration (MBEC) of the bioactive agent.

BRIEF DESCRIPTION OF THE DRAWINGS

FIG. 1 illustrates a multi-well-based cell culture test device according to one embodiment of the present invention.

FIG. 2 illustrates a cross-sectional view of a well unit of a multi-well-based cell culture test device according to one embodiment of the present invention.

FIG. 3 illustrates a cross-sectional view of a well unit of a multi-well-based cell culture test device according to one embodiment of the present invention.

FIG. 4 shows an antibiotic testing process using a cell culture test device according to one embodiment of the present invention.

FIG. 5 shows loading of a sample into a first sub-well of a cell culture test device according to one embodiment of the present invention.

FIG. 6 shows a focus mark provided on the underside of a first sub-well of a cell culture test device according to one embodiment of the present invention.

FIG. 7 shows the growth of reference strain *E. coli* ATCC 25922 without antibiotics, which was observed at regular time intervals using a cell culture test device according to one embodiment of the present invention.

FIG. 8 shows a process for susceptibility testing of reference strain *E. coli* ATCC 25922 to ceftazidime as an antibiotic, which was observed at regular time intervals using a cell culture test device according to one embodiment of the present invention.

FIG. 9 shows a process for susceptibility testing of reference strain *S. aureus* ATCC 29213 to ampicillin as an antibiotic, which was observed at regular time intervals using a cell culture test device according to one embodiment of the present invention.

FIG. 10 shows a process for susceptibility testing of reference strain *P. aeruginosa* ATCC 27853 to aztreonam as an antibiotic, which was observed at regular time intervals using a cell culture test device according to one embodiment of the present invention.

FIG. 11 shows a process for susceptibility testing of reference strain *E. faecalis* ATCC 29212 to tetracycline as an antibiotic, which was observed at regular time intervals using a cell culture test device according to one embodiment of the present invention.

FIG. 12 shows results of susceptibility testing of gram negative strains *Klebsiella pneumoniae, Enterobacter aerogenes*, and *P. aeruginosa* obtained from four blood samples to antibiotics, which was observed using a cell culture test device according to one embodiment of the present invention.

FIG. 13 shows results of susceptibility testing of gram positive strains *Staphylococcus epidermis, Enterococcus faecium*, and *Staphylococcus haemolyticus* obtained from four blood samples to antibiotics, which was observed using a cell culture test device according to one embodiment of the present invention.

MODE FOR CARRYING OUT THE INVENTION

Embodiments of the present invention will now be described in detail with reference to the accompanying drawings. However, the present invention may be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the dimensions, such as widths and thicknesses, of elements may be exaggerated for clarity. The drawings are explained from an observer's point of view. It will be understood that when an element is referred to as being "on" another element, it can be directly on the other element, or one or more intervening elements may also be present therebetween. Those skilled in the art will appreciate that many modifications can be made without departing from the spirit of the invention. Throughout the accompanying drawings, the same reference numerals are used to designate substantially the same elements.

On the other hand, terms used herein are to be understood as described below. While such terms as "first" and "second," etc., may be used to describe various elements, such elements must not be limited to the above terms. The above terms are used only to distinguish one element from another. For example, a first element may be referred to as a second element, and likewise a second element may be referred to as a first element.

As used herein, the singular forms "a", "an" and "the" are intended to include the plural forms as well, unless the context clearly indicates otherwise. It will be further understood that the terms "include(s)", "including", "have (has)" and/or "having", when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Respective steps of the methods described herein may be performed in a different order than that which is explicitly described. In other words, the respective steps may be performed in the same order as described, simultaneously, or in a reverse order.

FIG. 1 illustrates a multi-well-based cell culture test device according to one embodiment of the present invention. In FIG. 1, (a) is a perspective view of the multi-wellbased cell culture test device and (b) is a partially enlarged view of the multi-well-based cell culture test device.

Referring to FIG. 1, the multi-well-based cell culture test device 100 has an array structure of a plurality of aligned well units 110. Each of the well units 110 includes a first sub-well 120 adapted to accommodate a first fluid, a second sub-well 130 adapted to accommodate a second fluid, and a barrier 140 located between the first sub-well and the second sub-well to partition the first sub-well and the second sub-well. The plurality of aligned well units 110 may have substantially the same dimensions as the wells of a commercial multi-well plate. The centers of the well units 110 may coincide with the centers of the wells of a commercial multi-well plate.

Multi-well plates are standard tools for treating and analyzing a large number of samples in chemical, biochemical and/or biological assays. Multi-well plates may take various forms, sizes and shapes. Generally, multi-well plates are produced to have standard sizes and shapes and have standard arrangements of wells. The standard arrangements of wells include those found in 96-well plates (12×8 array of wells), 384-well plates (24×16 array of wells), and 1536-well plates (48×32 array of wells). Multi-well plates having other arrangements of wells are commercially available. The cell culture test device 100 is readily compatible with various conventional biological analysis techniques because its dimensions are similar to those of a commercial multi-well plate.

Each of the first fluid and the second fluid may usually include at least 80% or 90% by weight of water as a dispersion medium or solvent. For example, the first fluid may be a mixture solution of a gelling agent-containing liquid medium and a biological agent. The second fluid may be, for example, a solution containing a bioactive agent or a solvent capable of dissolving a bioactive agent.

FIG. 2 illustrates a cross-sectional view of a well unit 210 of a multi-well-based cell culture test device according to one embodiment of the present invention. In FIG. 2, (a) is a plan view of the well unit 210 of the cell culture test device and (b) is a cross-sectional view taken along line A-A' of (a). The well unit 210 includes a first sub-well 220 in the form of a well that has a space sufficient to accommodate the first fluid. The volume of the well is not especially limited as long as the well has a size sufficient to observe responses of cells present in the loaded first fluid for a long time. For example, the volume of the well may be from 100 μl to 2000 μl.

The first sub-well 220 may have a recess in the depth direction with respect to its bottom to accommodate a solid thin film formed by solidifying the first fluid. The recess 221 may have a circular or elliptical shape in cross section. Alternatively, the recess 221 may have a tetragonal, pentagonal or hexagonal shape in cross section. The ratio of the width w1 of the recess 221 to the width w2 of the first sub-well 220 may be from 0.5:1 to <1:1. The shape of the recess and the ratio of the width of the recess to the width of the first sub-well are not particularly limited as long as well has a size sufficient to observe responses of cells present in the loaded first fluid for a long time. Preferably, the recess has a circular shape in cross section. The ratio of the width w1 of the recess 221 to the width w2 of the first sub-well 220 is preferably from 0.2:1 to 0.99:1, more preferably from 0.4:1 to 0.8:1, most preferably from 0.55:1 to 0.65:1. If the ratio of the width of the recess to the width of the first sub-well is <0.2:1, the volume of the recess is too small to accommodate the first fluid, making it difficult to observe cells. Meanwhile, if the ratio of the width of the recess to the width of the first sub-well is >0.99:1, the recess may be substantially impossible to form.

At least a portion of the bottom of the recess may be made of an optically transparent material such that analytes present in the first fluid are observable through the bottom of the recess. For example, the body of the cell culture test device may be made of a transparent material. The transparent material is preferably a polymer resin such as polystyrene, polyethylene, polypropylene, polymethacrylate or polycarbonate. The cell culture test device may be manufactured by injection molding the polymer resin.

In FIG. 3, (a) illustrates a well unit 310 of a multi-well-based cell culture test device according to one embodiment of the present invention and (b) illustrates a cross-sectional view taken along line A-A' of (a). Referring to FIG. 3, at least one micropatterned groove 322 may be formed at the bottom of a recess 321. The micropatterned groove 322 serves to well fix a first fluid to the bottom of the recess 321 by capillary action. The micropatterned groove 322 may have a circular or elliptical shape in cross section. Alternatively, the micropatterned groove 322 may have a polygonal shape such as a square, a pentagon and a hexagon in cross section. The micropatterned groove 322 may be provided in plurality at the bottom of the recess 321. In this case, the micropatterned grooves 322 may take the form of microwells or microchannels spaced apart from each other. For example, the micropatterned groove 322 may be a doughnut-shaped microchannel, as illustrated in (b) of FIG. 3, and may have the dimensions defined in (c) of FIG. 3. For example, the micropatterned groove 322 may have of 500 μm to 1.5 mm and a depth (or thickness) of 200 μm. These dimensions facilitate subsequent imaging, enable uniform spreading of the first fluid in the first sub-well 320 by capillary action, and allow the first fluid to be well fixed to the micropatterned groove or the recess. The micropatterned groove is preferably shaped such that cells can be easily observed. The first fluid may be a liquid medium containing a gelling agent. In this case, the first fluid is gelled after the lapse of a predetermined time, resulting in the formation of a solid thin film filling the recess 121 including the micropatterned groove 122.

Referring back to FIG. 1, the second sub-well 130 may be in the form of a well that has a space sufficient to accommodate the second fluid. The second sub-well may include a bioactive agent in the form of a freeze-dried solid. In this case, the bioactive agent can be dissolved by the second fluid loaded into the second sub-well, with the result that a solution of the bioactive agent can be prepared.

The barrier 140 may be located between the first sub-well 120 and the second sub-well 130 to partition the first sub-well 120 and the second sub-well 130. The barrier 140 has such a height that the first fluid does not overflow into the second sub-well 130 when the first fluid is loaded into the first sub-well 120 to fill the recess 121. The barrier prevents the first fluid from overflowing into the second sub-well so that contamination of the first fluid with the second sub-well including the solid bioactive agent can be prevented. Since analytes present in the first fluid come into contact with the bioactive agent after being gelled by the gelling agent of the first fluid, the presence of the barrier enables sequential cell culture testing. At the same time, the barrier 140 has such a height that the second fluid loaded into the second sub-well overflows into the first sub-well 120.

FIG. 4 shows an antibiotic testing process using a cell culture test device according to one embodiment of the present invention.

Referring first to (a) of FIG. 4, a liquid medium containing a gelling agent is mixed with a biological agent to prepare a mixture solution as a first fluid. The liquid medium may include at least about 95% by weight of water and can be solidified due to the presence of the gelling agent. As the gelling agent, there may be exemplified agar, agarose, gelatin, alginate, collagen or fibrin. The use of agar or agarose is preferred. For example, agar may be used in an amount of 0.5 to 4% by weight in the liquid medium. The liquid medium usually requires no nutrients. In some examples, however, the liquid medium may include nutrients. The liquid medium may be a solution including a medium stimulating the division of particular cells.

Examples of suitable biological agents include viruses, bacteria, fungi, algae, protozoa, parasitic pathogens, human and mammalian cells, and biofilms. The biological agent may be a mixture of an infectious biological agent, such as a bacterial, viral or fungal strain, and blood cells. For example, the biological agent may be blood collected from a human infected with bacteria. In this case, a medium stimulating the division of only the bacterial cells can be used to distinguish the bacterial cells from the blood cells based on different sizes of the bacterial cells and the blood cells. The biological agent may grow in a liquid or solid medium and the growth thereof may be affected by the kind and concentration of a foreign bioactive agent. The density of the biological agent in the mixture solution is from $10^2$ to $10^{10}$ cells/ml, preferably from $10^4$ to $10^{10}$ cells/ml, more preferably from $10^5$ to $10^9$ cells/ml. If the density of the biological agent is below the lower limit, it may be difficult to perceive the location of the biological agent. Meanwhile, if the density of the biological agent exceeds the upper limit, it may be difficult to perceive the individual state of the biological agent.

Referring next to (b) of FIG. 4, the mixture solution is provided to a recess 421 formed at the bottom of a first sub-well. The mixture solution may be loaded in an amount corresponding to the volume of the recess of the first sub-well. The volume of the mixture solution loaded into the recess of the first sub-well is preferably from 10 µl to 200 µl, more preferably from 10 µl to 150 µl. If the volume of the mixture solution loaded into the first sub-well is less than the lower limit, the density of cells in the mixture solution is low, making it difficult to observe the cells. Meanwhile, if the volume of the mixture solution loaded into the first sub-well exceeds the upper limit, the mixture solution may overflow into a second sub-well beyond a barrier. The formation of at least one micropatterned groove 422 at the bottom of the recess is effective in uniformly spreading the first fluid over the entire region of the recess by capillary action. The micropatterned groove also allows the mixture solution to be well fixed to the desired area. FIG. 5 shows loading of a sample into a first sub-well 520 of a cell culture test device according to one embodiment of the present invention. Referring to FIG. 5, a micropatterned groove 522 is formed in the well a sample to fix the sample to only the desired area.

As shown in (b) of FIG. 4, the mixture solution may be a mixture of an infectious biological agent, such as a bacterial strain, and blood cells. For example, the mixture solution may include a culture of blood collected from a human infected with bacteria, i.e. a culture of blood positive for bacterial infection. In this case, a liquid medium stimulating the division of only the bacterial cells can be used to distinguish the bacterial cells from the blood cells based on different sizes of the bacterial cells and the blood cells. Examples of media capable of stimulating the division of only bacterial cells include Mueller-Hinton broth (MHB), Mueller-Hinton agar (MHA), Luria-Bertani broth (LBB), and Luria-Bertani agar (LBA).

A blood sample positive for bacterial infection is collected and diluted with a medium containing a gelling agent. At this time, there is no need to separate the bacteria from the blood sample before testing, contributing to testing time reduction.

The mixture solution is solidified to form a solid thin film immobilized with the biological agent. When the temperature of the liquid medium drops, the medium is solidified, which restricts the mobility of the biological agent. This immobilization facilitates continuous observation of the motile biological agent.

The cell culture test device or the bottom of the recess is preferably made of a transparent material for optical imaging. Referring again to FIG. 3, the liquid medium is coated on the recess 321 of the first sub-well of the cell culture test device and is solidified to form a solid thin film. The thickness of the solid thin film is determined depending on the depth of the recess 321. The depth of the recess may be in the range of 1 µm to 5 mm, 1 µm to 3 mm, 1 µm to 2 mm, 1 µm to 1.5 mm, 1 µm to 1 mm, 1 µm to 800 µm, 1 µm to 500 µm, 1 µm to 100 µm, 10 µm to 3 mm, 100 µm to 500 µm, 10 µm to 1 mm, 100 µm to 1 mm, 200 µm to 1 mm, 500 µm to 1 mm or 100 µm to 500 µm. Preferably, the depth of the recess is from 100 µm to 500 µm. Within the depth range of the recess defined above, the biological agent immobilized into the recess can be easily observed on a single cell or single cell colony basis.

The width of the recess 321 may be from 100 µm to 5 mm, from 300 µm to 5 mm, from 500 µm to 3 mm or from 1 mm to 3 mm when the size of an imaging area is taken into consideration. Preferably, the width of the recess is in the range of 1 mm to 3 mm. Within this range, the recess of the first sub-well can provide a space where cells are immobilized on the desired area. In addition, the entire region of the recess can be observed because the dimensions of the recess are not larger than those of an imaging system.

The shape and width of the recess are not especially limited as long as the largest possible amount of the mixture solution (including the gelling agent and the biological agent-containing liquid medium) can be loaded while maintaining the dimensions and width, which facilitates accurate control over responses to the bioactive agent. It is desirable that the dimensions of the recess are not larger than those of an imaging system, because the entire region of the recess can be observed without the need to move the cell culture test device.

The thickness and width of the solid thin film are determined depending on the depth and width of the recess. As used herein, the term "thin film" refers to a thin layer that has a thickness sufficient to immobilize the biological agent and to observe the single cells or single cells colonies. The thickness of the thin film is typically in the range of 1 µm to 5 mm, 1 µm to 3 mm, 1 µm to 2 mm, 1 µm to 1.5 mm, 1 µm to 1 mm, 1 µm to 800 µm, 1 µm to 500 µm, 1 µm to 100 µm, 10 µm to 3 mm, 100 µm to 500 µm, 10 µm to 1 mm, 100 µm to 1 mm, 200 µm to 1 mm or 500 µm to 1 mm, but is not particularly limited to this range. The thickness of the solid thin film may correspond to the size of a side of the solid thin film in a direction perpendicular to a side of the solid thin film to be observed. Within the thickness range of the solid thin film defined above, the biological agent immobilized in the solid thin film can be observed on a single cell or single cell colony basis.

A focus mark 623 may be provided on the underside of the first sub-well to provide information on the position of analytes. FIG. 6 shows a focus mark provided on the underside of a first sub-well of a cell culture test device according to one embodiment of the present invention. Referring to FIG. 6, the focus mark 623 may be marked on the underside of the first sub-well such that a target area of the cell culture test device can be automatically tracked. The focus mark is provided in the form of a microchannel by injection molding. Since the biological agent is immobilized in the solid thin film, the use of the focus mark 623 enables imaging of the same area every time pictures are taken. The focus mark serves to correct the positions of analytes in the three axial directions, i.e. x-, y-, and z-axis directions, in the aforementioned automatic tracking of a target area.

As shown in (c) of FIG. 4, a second sub-well 430 including a bioactive agent in a solid form is provided with a solvent capable of dissolving the bioactive agent. When a bioactive agent is absent in the second sub-well 430, a solution containing a bioactive agent can be provided to the second sub-well 430. Herein, the bioactive agent may include a substance selected from antibiotics, anticancer agents, drugs such as immunosuppressants, nutrients, cellular secretions, signal transducers, viruses, cells, micro RNAs, proteins, antigens, antibodies, and DNA. The second sub-well may include a bioactive agent in a solid form, as shown in (b) of FIG. 4. In this case, the bioactive agent may be in the form of a freeze-dried solid. The solvent capable of dissolving the freeze-dried bioactive agent may be selected from water, cell culture media, dimethylformamide (DMF), and dimethyl sulfoxide (DMSO). The solvent may be introduced by pipetting such that the solid bioactive agent is completely dissolved and the resulting solution has a uniform concentration.

Next, as shown in (c) of FIG. 4, the solvent capable of dissolving the bioactive agent is loaded in such an amount that it crosses over the barrier 440, to allow the bioactive agent to diffuse into the solid thin film in the first sub-well 420. Also, when the bioactive agent is absent in the second sub-well 430, the solution containing the bioactive agent is loaded in such an amount that it crosses over the barrier, to allow the bioactive agent to diffuse into the solid thin film in the first sub-well 420. The volume of the solution containing the bioactive agent or the solvent capable of dissolving the bioactive agent loaded into the second sub-well 430 is not limited as long as the solution containing the bioactive agent crosses over the barrier 440 to form an interface with the solid thin film formed in the first sub-well 420. The volume is preferably from 50 µl to 200 µl, more preferably from 75 µl to 125 µl.

Next, as shown in (d) of FIG. 4, responses of the biological agent to the bioactive agent are observed. The solution including the bioactive agent diffuses into the solid thin film through the interface with the solid thin film and meets the biological agent immobilized in the solid thin film. The biological agent immobilized in the solid thin film is widely distributed in the horizontal direction with respect to the observation direction, and as a result, the biological agent can be observed on a single cell or single cell colony basis. According to the testing method of the present invention, changes in the growth of single bacteria can be generally observed within several tens of minutes (normally 30 minutes) and those of single colonies of bacteria can be typically observed within 4 to 6 hours. Accordingly, the testing method of the present invention allows for the identification of the effect of the bioactive agent on the biological agent in a more accurate and rapid manner than conventional testing methods. For example, when the bioactivity of the bioactive agent on bacterial cells is tested, the test can be completed within 3 to 4 hours. The testing method of the present invention can be used to observe changes in the morphology of single cells or changes of single cell colonies in the presence of various antibiotics by time-lapse imaging.

Responses of the biological agent to the bioactive agent can be observed on a single cell colony basis to determine the minimum inhibitory concentration (MIC) or minimum biofilm eradication concentration (MBEC) of the bioactive agent. The cell culture test device of the present invention is very useful for biofilm assay as well as antibiotic susceptibility testing. Biofilms are found in areas infected with microbes or to which microbes are attached. Biofilms refer to films that constitute mucilaginous microbial complexes, which are formed by microbes surrounded by polymer matrices. The formation of biofilms can greatly affect human health. Biofilms cause pulmonary infections, otitis media, periodontitis, and other infectious diseases. The resistance of bacteria present in biofilms to antibiotics is at least 1,000 times stronger than that of suspended bacteria. Flow cell systems and well-based systems have been used to investigate biofilms. However, these assay systems require a long time of several days for biofilm formation. Other difficulties associated with the use of the assay systems are that biofilms need to be stained and confocal microscopes should be used for observation. Further experiments are needed for the measurement of minimum inhibitory concentration (MIC) or minimum biofilm eradication concentration (MBEC). Such systems are very large in size and they fail to clearly show biofilm formation stages and to represent in vivo biofilm formation.

Thus, there is a need for efficient systems that are suitable to investigate the formation of biofilms and the reactivity of biofilms with antibiotics. In consideration of this need, the cell culture test device according to one embodiment of the present invention proves to be an excellent alternative to conventional test devices.

An optical measurement system may be used for observation. The optical measurement system may include an imaging system, such as a CCD or CMOS camera. The optical measurement system may include optical units or devices necessary for focusing and light imaging, such as a lens, an illuminator, and a light guide. The optical measurement system may include an image processing system for processing and analyzing image data observed by the imaging system. The optical measurement system rapidly records and analyzes changes in the growth of the biological agent observed during testing to obtain test results. The central portion of the first sub-well where the gelled first fluid forms an interface with the second fluid becomes an imaging area. The imaging area may have a size of about 400 µm×800 µm to about 800 µm×1600 µm.

Consequently, the use of the testing method based on the immobilization of the biological agent and the diffusion of the bioactive agent can greatly reduce the amounts of drugs and cells necessary for drug testing, and enables rapid tracking of changes in the growth of single cells or single cell colonies to obtain test results on the drugs as rapidly as 2 hours (normally within 6 hours), compared to the prior art. This is the most rapid testing speed known thus far.

FIG. 7 shows growth of reference strain E. coli ATCC 25922 without antibiotics, which was observed at regular time intervals using a cell culture test device according to one embodiment of the present invention. The bacterial colonies increased in size with time. The colonies of the strain were visible to the naked eye from 4 h after initiation of colonization.

FIG. 8 shows a process for susceptibility testing of reference strain *E. coli* ATCC 25922 to ceftazidime as an antibiotic, which was observed at regular time intervals using a cell culture test device according to one embodiment of the present invention. The antibiotic was used at concentrations of 0.25 µg/ml to 4.0 µg/ml recommended by the Clinical & Laboratory Standards Institute (CLSI). The results were recorded at 2 h intervals until 6 h after initiation of testing. The minimum inhibitory concentration (MIC) of the antibiotic, an important factor in antibiotic susceptibility testing, could be determined, as shown in FIG. 8.

FIG. 9 shows a process for susceptibility testing of reference strain *S. aureus* ATCC 29213 to ampicillin as an antibiotic, which was observed at regular time intervals using a cell culture test device according to one embodiment of the present invention. Colonies of *S. aureus* ATCC 29213 began to be observed in the presence of 0.25 µg/ml ampicillin from 2 h after initiation of testing. The colonies increased in size and were made clear at 6 h after initiation of testing. Colonies were observed later in the presence of 0.5 µg/ml ampicillin than in the presence of 0.25 µg/ml ampicillin. Clear colonies were observed 6 h after initiation of testing. The MIC of the antibiotic against *S. aureus* ATCC 29213 was found to be 1.0 µg/ml.

FIG. 10 shows a process for susceptibility testing of reference strain *P. aeruginosa* ATCC 27853 to aztreonam as an antibiotic, which was observed at regular time intervals using a cell culture test device according to one embodiment of the present invention. Colonies of *P. aeruginosa* ATCC 27853 were clearly observed in the presence of 1.0 and 2.0 µg/ml aztreonam 6 h after initiation of testing. Smaller colonies were observed even in the presence of 4.0 µg/ml aztreonam 6 h after initiation of testing. The MIC of the antibiotic against *P. aeruginosa* ATCC 27853 was found to be 8.0 µg/ml.

FIG. 11 shows a process for susceptibility testing of reference strain *E. faecalis* ATCC 29212 to tetracycline as an antibiotic, which was observed at regular time intervals using a cell culture test device according to one embodiment of the present invention. Small but clear colonies of the strain were observed in the presence of 4.0 µg/ml tetracycline 6 h after initiation of testing. The MIC of the antibiotic against *E. faecalis* ATCC 29212 was found to be 8.0 µg/ml.

FIG. 12 shows results of susceptibility testing of gram negative strains *Klebsiella pneumoniae*, *Enterobacter aerogenes*, and *P. aeruginosa* obtained from four blood samples to antibiotics, which was observed using a cell culture test device ("DRAST") according to one embodiment of the present invention. The tests were conducted on various antibiotics that are currently used in testing organizations. A conventional testing method based on broth microdilution (BMD) and the testing method using the cell culture test device according to the present invention were used to test the susceptibility of the strains to the antibiotics, and the results were compared. *E. aerogenes* was susceptible (S) to colistin in the BMD testing method and showed an intermediate resistance (I) to colistin in the testing method using the cell culture test device (DRAST) of the present invention. *P. aeruginosa* showed intermediate resistances (I) to ticarcillin, ticarcillin/clavulanic acid, cefotaxime, aztreonam, and trimethoprim/sulfamethoxazole in the BMD testing method but was susceptible to the same antibiotics in the testing method using the cell culture test device of the present invention. *P. aeruginosa* was susceptible to colistin in the BMD testing method and showed an intermediate resistance (I) to colistin in the testing method using the cell culture test device of the present invention. The strains showed different responses (i.e. susceptibility (S) vs. intermediate resistance (I)) to the above-mentioned antibiotics in the BMD testing method and the testing method using the cell culture test device of the present invention. Accordingly, these test results are all classified as minor errors. The results of *K. pneumoniae* on all antibiotics in the BMD testing method were in good agreement with the results obtained in the testing method using the cell culture test device of the present invention. The concentrations shown in FIG. 12 are expressed in µg/mL.

FIG. 13 shows results of susceptibility testing of gram positive strains *Staphylococcus epidermis*, *Enterococcus faecium*, and *Staphylococcus haemolyticus* obtained from four blood samples to antibiotics, which was observed using a cell culture test device (DRAST) according to one embodiment of the present invention. The tests were conducted on various antibiotics that are currently used in testing organizations. A conventional testing method based on broth microdilution (BMD) and the testing method using the cell culture test device according to the present invention were used to test the susceptibility of the strains to the antibiotics, and the results were compared. The results of *S. epidermis* on oxacillin, ciprofloxacin, linezolid, levofloxacin, and trimethoprim/sulfamethoxazole were found to be different from the results obtained in the testing method using the cell culture test device of the present invention. However, the results of *S. epidermis* on the antibiotics other than trimethoprim/sulfamethoxazole are classified as minor errors. *S. haemolyticus* belonging to the same *Staphylococcus* genus as *S. epidermis* showed different results on ampicillin, tetracycline, clindamycin, levofloxacin, and imipenem in the BMD testing method and the testing method using the cell culture test device of the present invention. However, the results of *S. haemolyticus* on the antibiotics other than ampicillin are classified as minor errors. The results of *S. haemolyticus* on the antibiotics other than the above-mentioned antibiotics in the BMD testing method were in good agreement with the results obtained in the testing method using the cell culture test device of the present invention.

One of the two *E. faecium* strains isolated from different samples showed different responses (i.e. susceptibility (S) vs. intermediate resistance (I) or intermediate resistance (I) vs. resistance (R)) to rifampicin, linezolid, and vancomycin in the BMD testing method and the testing method using the cell culture test device of the present invention. Accordingly, these results are classified as minor errors. The other *E. faecium* strain showed the same susceptibility results to the antibiotics other than trimethoprim/sulfamethoxazole in the BMD testing method and the testing method using the cell culture test device of the present invention. The concentrations shown in FIG. 13 are expressed in µg/mL.

Based on the results in FIGS. 12 and 13, it was found that the minor errors of the antibiotic susceptibility results obtained in the testing method using the cell culture test device of the present invention were at most 10%, which complies with FDA recommendations, unlike those obtained in the BMD testing method. In conclusion, the cell culture test device of the present invention can be used in clinical applications. In addition, the use of the cell culture test device according to the present invention can reduce the time required for testing and can reduce the amounts of reagents and cells necessary for testing. According to the conventional antibiotic testing method, filter disks containing an antibiotic were placed on an agar plate into which bacteria were inoculated. The susceptibility of the bacteria was confirmed by measuring the diameters of clear zones around the antibiotic filter disks after passage of 16-24 hr. In contrast, the use of the cell culture test device according to the present invention can greatly reduce the amounts of drugs and cells necessary for drug testing and enables rapid tracking of changes in the growth of single cells or single cells colonies to obtain test results on the drugs as rapidly as 2 hours (normally within 6 hours), compared to the prior art. When the susceptibilities of one type of cell to various kinds of antibiotics at different concentrations are tested, the conventional antibiotic susceptibility testing method requires tens of agar plates while the testing method of the present invention requires a smaller number of plates because it can be conducted in the wells of the cell culture test device.

Therefore, the cell culture test device of the present invention is very economical because its use can reduce the time for analysis, researchers' efforts, the amount of bioactive agents, the amount of media, and the number of plates.

Although the present invention has been described in detail with reference to the drawings and embodiments, those skilled in the art will appreciate that various variations and modifications can be made to the embodiments without departing from the spirit of the present invention as disclosed in the appended claims.

The invention claimed is:

1. A multi-well-based cell culture test device having an array structure of a plurality of aligned well units, each of which comprises a first sub-well adapted to accommodate a first fluid, a second sub-well adapted to accommodate a second fluid, and a barrier region located between and directly contacting the first sub-well and the second sub-well,
wherein,
the first sub-well has a first bottom surface and a recess located at a center of the first bottom surface and the recess is configured to accommodate a solid thin film formed by solidifying the first fluid,
the second sub-well has a second bottom surface,
the barrier region consists of a barrier bottom surface and two sidewalls,
a level of the barrier bottom surface is higher than a level of the first bottom surface and a level of the second bottom surface such that the first fluid does not overflow into the second sub-well when the first fluid is loaded into the first sub-well to fill the recess,
the first bottom surface is flat.

2. The multi-well-based cell culture test device according to claim 1, wherein at least one micropatterned groove is formed at the bottom of the recess.

3. The multi-well-based cell culture test device according to claim 2, wherein the micropatterned groove is provided in plurality and the micropatterned grooves are channels arranged concentrically around the center of the recess.

4. The multi-well-based cell culture test device according to claim 1, wherein at least a portion of the bottom of the recess is made of an optically transparent material such that analytes present in the first fluid are observable through the bottom of the recess.

5. The multi-well-based cell culture test device according to claim 1, wherein a focus mark is provided on the underside of the first sub-well to provide information on the position of analytes.

6. The multi-well-based cell culture test device according to claim 1, wherein the ratio of the width of the recess to the width of the first sub-well is from 0.2:1 to 0.99:1.

7. The multi-well-based cell culture test device according to claim 1, wherein the dimensions of each of the well units correspond to those of each well of a commercial multi-well plate.

8. The multi-well-based cell culture test device according to claim 7, wherein the well units are arranged in a 1×1, 1×2, 1×4, 2×4, 4×6, 12×8, 24×16 or 48×32 matrix.

9. The multi-well-based cell culture test device according to claim 1, wherein the first fluid is a mixture solution of a gelling agent-containing liquid medium and a biological agent.

10. The multi-well-based cell culture test device according to claim 1, wherein the second fluid is a solution containing a bioactive agent.

11. The multi-well-based cell culture test device according to claim 1, wherein the second sub-well comprises a bioactive agent in a solid form.

12. The multi-well-based cell culture test device according to claim 11, wherein the second fluid is a solvent capable of dissolving the bioactive agent.

13. The multi-well-based cell culture test device according to claim 1,
wherein each of the well units has only one first sub-well and only one second sub-well.

14. The multi-well-based cell culture test device according to claim 1,
wherein the barrier bottom surface constitutes a bottom surface of each of the plurality of the aligned well units.

* * * * *